(12) United States Patent
Ozer et al.

(10) Patent No.: US 8,431,753 B2
(45) Date of Patent: Apr. 30, 2013

(54) CONVERSION OF BUTANOL TO A REACTION PRODUCT COMPRISING 2-ETHYLHEXANOL USING HYDROXYAPATITE CATALYSTS

(75) Inventors: Ronnie Ozer, Arden, DE (US); Paul Joseph Fagan, Wilmington, DE (US); Thomas G. Calvarese, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 229 days.

(21) Appl. No.: 13/043,834

(22) Filed: Mar. 9, 2011

(65) Prior Publication Data

US 2012/0232314 A1 Sep. 13, 2012

(51) Int. Cl.
*C07C 29/34* (2006.01)

(52) U.S. Cl.
USPC .......................... 568/905; 568/902; 568/902.2

(58) Field of Classification Search .................. 568/905, 568/902, 902.2
See application file for complete search history.

(56) References Cited

U.S. PATENT DOCUMENTS

| 3,558,716 A | 1/1971 | Engelhardt et al. |
| 6,323,383 B1 | 11/2001 | Tsuchida et al. |
| 2007/0255079 A1 | 11/2007 | Tsuchida et al. |
| 2008/0025903 A1 | 1/2008 | Cortright |
| 2008/0216391 A1 | 9/2008 | Cortright et al. |
| 2008/0300434 A1 | 12/2008 | Cortright et al. |
| 2008/0300435 A1 | 12/2008 | Cortright et al. |

FOREIGN PATENT DOCUMENTS

| GB | 655864 | 8/1948 |
| GB | 949156 | 11/1962 |
| JP | 31005325 B4 | 7/1956 |
| WO | 2009/034719 | 3/2009 |
| WO | 2009/064828 | 5/2009 |
| WO | 2009/205246 | 5/2009 |
| WO | 2011/021232 A1 | 2/2011 |
| WO | 2011/031029 | 3/2011 |

OTHER PUBLICATIONS

Carlini et al., Selective Synthesis of 2-ethyl-1-hexanol from n-butanol through the Guerbet Reaction by Using Bifunctional Catalysts Based on Cooper or Palladium Precursors and Sodium Butoxide, J. of Molecular Catalysis A: Chemical 212 Issues 1-2, (2004) 65-70.
International Search Report and Written Opinion, International Application No. PCT/US 10/48369, Mailed: Nov. 16, 2010.
J. Logsdon, Guerbet Reaction, in Kirk-Othmer Encyclopedia of Chemical Tech., John Wiley and Sons, Inc., NY, 2001.
S. Sugiyama et al., Phos. Res. Bulletin, vol. 8, pp. 23-30 (1998).
G. George et al, Material Science, vol. 22, pp. 2274-2276 (1987).
A. Yasukawa et al, J. Colloid Interface Sci., vol. 191, pp. 407-415 (1997).
O. Fujino, Bulletin of the Chem. Soc. of Japan, vol. 48(5), 1455-1458 (1975).
S.-C. Liou et al., Biomaterials, vol. 25, pp. 189-196, (2004).
H. Scott Folger, Elements of Chemical Reaching Engineering, 2nd Edition (1992), Prentice-Hall Inc, CA (Book).
T. Tsuchida et al., Industrial Engineering Chemical Research, vol. 47, pp. 1443-1452, (2008).
Sugiyama et al., Journal of Molecular Catalysis A:Chemical 135, pp. 199-208, (1998).
Tsuchida et al., Industrial Engineering Chemical Research, vol. 45, pp. 8634-8642, (2006).
C. Wei et al., Catalysis Communications, vol. 9, pp. 516-521, (2008).
T. Tsuchida et al., Journal of the Japan Petroleum Institute, vol. 52, (2), pp. 51-59 (2009).
T. Tsuchida et al., Journal of Catalysis 259, pp. 183-189, (2008).
J. Logsdon, "Guerbet Reaction" in Kirk-Othmer Encycl. of Chem. Tech., John Wiley and Sons, Inc., New York (2001).

*Primary Examiner* — Elvis O Price
(74) *Attorney, Agent, or Firm* — Kevin S. Dobson

(57) ABSTRACT

Catalytic processes to produce a reaction product comprising 2-ethylhexanol by contacting a reactant comprising 1-butanol with a catalyst composition under suitable reaction conditions are provided. The catalyst composition may comprise a hydroxyapatite of the Formula $(M_wM'_xM''_yM'''_z)_5(PO_4)_3(OH)$, wherein M is Mg; M' is Ca; M" is Sr; M''' is Ba; w is any number between 0 and 1 inclusive; x is any number from 0 to less than 0.5; y is any number between 0 and 1 inclusive; z is any number between 0 and 1 inclusive; and $w+x+y+z=1$. Base-treated catalyst compositions may be used.

14 Claims, No Drawings

CONVERSION OF BUTANOL TO A REACTION PRODUCT COMPRISING 2-ETHYLHEXANOL USING HYDROXYAPATITE CATALYSTS

FIELD OF THE INVENTION

The present invention relates to processes for the catalytic conversion of 1-butanol to a reaction product comprising 2-ethyl-1-hexanol using hydroxyapatite catalyst compositions.

BACKGROUND

2-Ethylhexanol, a branched chain alcohol, is used in the manufacture of a variety of products due to its versatility as a chemical intermediate. For example, 2-ethylhexanol can be converted into a variety of useful esters or used as a chain terminator in the manufacture of condensation polymers.

Methods for producing 2-ethylhexanol from 1-butanol are known. For example, U.S. Pat. No. 3,558,716 discloses that according to the Guerbet reaction, beta-branched primary alcohols are obtained by reacting primary alcohols which in beta position to the hydroxyl group have a methylene ($CH_2$) group, in the presence of alkali and at elevated temperature. Equation (1) in the patent shows 2-ethylhexanol being formed from 1-butanol.

Carlini et al. disclose the selective synthesis of 2-ethyl-1-hexanol from n-butanol through the Guerbet reaction by using bifunctional catalysts based on copper or palladium precursors and sodium butoxide (Journal of Molecular Catalysis A: Chemical 212 (2004) 65-70).

Published US Patent Application 2007/0255079 A1 discloses a process for producing, from ethanol as a raw material, higher molecular weight alcohols having an even number of carbon atoms, such as 1-butanol, hexanol, octanol and decanol. The higher molecular weight alcohols are produced from ethanol using calcium phosphate-based compounds such as hydroxyapatite $Ca_{10}(PO_4)_6(OH)_2$, tricalcium phosphate $Ca_3(PO_4)_2$, calcium monohydrogen phosphate $CaHPO_4 \cdot (0\text{-}2)H_2O$, calcium diphosphate $Ca_2P_2O_7$, octacalcium phosphate $Ca_8H_2(PO_4)_6 \cdot 5H_2O$, tetracalcium phosphate $Ca_4(PO_4)_2O$, or amorphous calcium phosphate $Ca_3(PO_4)_2 \cdot nH_2O$ as a catalyst, the contact time being 0.4 second or longer.

Processes to produce 2-ethylhexanol from a reactant stream comprising 1-butanol continue to be sought. Particularly desired are vapor phase processes employing catalyst compositions which can provide good conversions of 1-butanol to 2-ethylhexanol with good selectivity while exhibiting long catalytic lifetimes and without the need to add base during the reaction to form 2-ethylhexanol. Such processes to produce 2-ethylhexanol are desired for the economic benefits they can offer.

SUMMARY OF THE INVENTION

The present invention provides catalytic processes for producing a reaction product comprising 2-ethylhexanol from a reactant comprising 1-butanol, using catalyst compositions comprising certain hydroxyapatite compositions.

In one aspect, the present invention is a process comprising the step of contacting a reactant comprising 1-butanol with a catalyst composition under suitable reaction conditions to produce a reaction product comprising 2-ethylhexanol, wherein;

(i) the suitable reaction conditions include a temperature of about 350° C. to about 425° C. and a pressure from about 0.1 MPa to about 20.7 MPa; and (ii) the catalyst composition comprises a hydroxyapatite of Formula (I):

$$(M_wM'_xM''_yM'''_z)_5(PO_4)_3(OH) \qquad (I)$$

wherein
M is Mg;
M' is Ca;
M" is Sr;
M'" is Ba;
w is any number between 0 and 1 inclusive;
x is any number from 0 to less than 0.5;
y is any number between 0 and 1 inclusive;
z is any number between 0 and 1 inclusive;
and w+x+y+z=1.

In one aspect, the present invention is a process comprising the step of contacting a reactant comprising 1-butanol with a base-treated catalyst composition under suitable reaction conditions to produce a reaction product comprising 2-ethylhexanol;

wherein the suitable reaction conditions include a temperature of about 350° C. to about 425° C. and a pressure from about 0.1 MPa to about 20.7 MPa; and wherein the base-treated catalyst composition is obtained by treating an initial catalyst composition comprising a hydroxyapatite of Formula (III):

$$(M_mM'_nM''_pM'''_q)_5(PO_4)_3(OH) \qquad (III)$$

wherein
M is Mg;
M' is Ca;
M" is Sr;
M'" is Ba;
m is any number between 0 and 1 inclusive;
n is any number between 0 and 1 inclusive;
p is any number between 0 and 1 inclusive;
q is any number between 0 and 1 inclusive;
and m+n+p+q=1 with a base at a treatment temperature from about 25° C. to about 300° C. for a treatment time of about 1 minute to about 24 hours, and optionally washing the isolated base-treated catalyst composition with a minimal amount of water.

In one aspect, the present invention is a process comprising the step:

contacting a reactant comprising 1-butanol with a base-treated catalyst composition under suitable reaction conditions to produce a reaction product comprising 2-ethylhexanol;

wherein the suitable reaction conditions include a temperature of about 350° C. to about 425° C. and a pressure from about 0.1 MPa to about 20.7 MPa; and wherein the base-treated catalyst composition is obtained by treating an initial catalyst composition comprising a hydroxyapatite of Formula (I):

$$(M_wM'_xM''_yM'''_z)_5(PO_4)_3(OH) \qquad (I)$$

wherein
M is Mg;
M' is Ca;
M" is Sr;
M'" is Ba;
w is any number between 0 and 1 inclusive;
x is any number from 0 to less than 0.5;
y is any number between 0 and 1 inclusive;
z is any number between 0 and 1 inclusive;
and w+x+y+z=1 with a base at a treatment temperature from about 25° C. to about 300° C. for a treatment time of about 1 minute to about 24 hours, and optionally washing the base-treated catalyst composition with a minimal amount of water.

DETAILED DESCRIPTION OF THE INVENTION

The present invention relates to catalytic processes for producing a reaction product comprising 2-ethylhexanol from a reactant comprising 1-butanol using catalyst compositions comprising certain hydroxyapatite compositions or catalyst compositions which have been treated with a base. Useful applications for the 2-ethylhexanol, which can be separated from the reaction product, include as a chemical intermediate in the manufacture of a variety of products, for example esters such as bis(2-ethylhexyl) phthalate.

Where the indefinite article "a" or "an" is used with respect to a statement or description of the presence of a step in a process of this invention, it is to be understood, unless the statement or description explicitly provides to the contrary, that the use of such indefinite article does not limit the presence of the step in the process to one in number.

Where a range of numerical values is recited herein, unless otherwise stated, the range is intended to include the endpoints thereof, and all integers and fractions within the range. It is not intended that the scope of the invention be limited to the specific values recited when defining a range.

The following definitions are used herein and should be referred to for interpretation of the claims and the specification.

The term "2-ethylhexanol" means 2-ethyl-1-hexanol.

The term "1-butanol conversion" means the chemical reaction of butanol to another compound.

The term "unreacted butanol" means butanol which has not been chemically reacted to another compound.

The term "elapsed time" means reaction time measured from the time when the reaction product comprising 2-ethylhexanol first exits the reactor.

The term "contacting" means bringing at least two things, such as an initial catalyst composition and a base, into physical contact.

The terms "Guerbet alcohol products" or "Guerbet alcohols" mean one or more alcohols produced by the Guerbet synthesis, wherein a primary or secondary alcohol having a methylene group at the α-position is condensed with itself, or with another alcohol also having a methylene group, to form a higher alcohol containing twice the number of carbon atoms of the single starting alcohol or, in the case of mixed alcohols, the sum of the number of carbon atoms in each reacting pair of alcohols. 2-Ethylhexanol is a Guerbet alcohol product of 1-butanol.

The term "base catalyst" means either a substance which has the ability to accept protons as defined by Brönsted, or a substance which has an unshared electron pair with which it can form a covalent bond with an atom, molecule or ion as defined by Lewis.

The term "wt %" means weight percent.
The term "° C." means degrees Celsius.
The term "g" means gram(s).
The term "min" means minute(s).
The term "h" means hour(s).
The term "mL" means milliliter(s).
The term "M" means molar.
The term "cm" means centimeter(s).
The term "MPa" means mega Pascal.
The term "GC" means gas chromatography.

Catalyst Composition:

In one embodiment of the process to produce a reaction product comprising 2-ethylhexanol, the catalyst composition comprises at least one hydroxyapatite based on unary, binary, tertiary, and quaternary combinations of magnesium, calcium, strontium, and barium cations. The catalyst composition comprises a hydroxyapatite of Formula (I):

$$(M_w M'_x M''_y M'''_z)_5(PO_4)_3(OH) \qquad (I)$$

where
M is Mg;
M' is Ca;
M'' is Sr;
M''' is Ba;
w is any number between 0 and 1 inclusive;
x is any number from 0 to less than 0.5;
y is any number between 0 and 1 inclusive;
z is any number between 0 and 1 inclusive;
and w+x+y+z=1.

With respect to M, M', M'', and M''', each of the metals is optional in the catalyst composition to the extent that at least one of the metals has to be present to conform to the above formulation.

In one embodiment, the catalyst composition comprises a hydroxyapatite of Formula (I) wherein w is 1, x is 0, y is 0, and z is 0. In one embodiment, the catalyst composition comprises a hydroxyapatite of Formula (I) wherein w is 0, x is 0, y is 1, and z is 0. In one embodiment, the catalyst composition comprises a hydroxyapatite of Formula (I) wherein w is 0, x is 0, y is 0, and z is 1.

In one embodiment, the catalyst composition comprises a hydroxyapatite of Formula (I) wherein w is any number between 0 and 1 inclusive; x is any number from 0 to less than 0.5; y is 0; and z is 0. In one embodiment, the catalyst composition comprises a hydroxyapatite of Formula (I) wherein w is any number between 0 and 1 inclusive; x is 0; y is any number between 0 and 1 inclusive; and z is 0. In one embodiment, the catalyst composition comprises a hydroxyapatite of Formula (I) wherein w is any number between 0 and 1 inclusive; x is 0; y is 0; and z is any number between 0 and 1 inclusive. In one embodiment, the catalyst composition comprises a hydroxyapatite of Formula (I) wherein w is 0; x is any number from 0 to less than 0.5; y is any number between 0 and 1 inclusive; and z is 0. In one embodiment, the catalyst composition comprises a hydroxyapatite of Formula (I) w is 0; x is any number from 0 to less than 0.5; y is 0; and z is any number between 0 and 1 inclusive. In one embodiment, the catalyst composition comprises a hydroxyapatite of Formula (I) wherein w is 0; x is 0; y is any number between 0 and 1 inclusive; and z is any number between 0 and 1 inclusive.

The catalyst composition may optionally further comprise at least one metal phosphate of Formula (II):

$$(M_a M'_b M''_c M'''_d)_3(PO_4)_2 \qquad (II)$$

where
M is Mg;
M' is Ca;
M'' is Sr;
M''' is Ba;
a is any number between 0 and 1 inclusive;
b is any number between 0 and 1 inclusive;
c is any number between 0 and 1 inclusive;
d is any number between 0 and 1 inclusive;
and a+b+c+d=1.

With respect to M, M', M", and M''', each of the metals is optional in the catalyst composition to the extent that at least one of the metals has to be present to conform to the above formulation.

The metal phosphate may comprise, for example, Mg, Ca, Sr, and Ba, or any three of these elements, or any two of these elements, or only one of these elements. In one embodiment, the catalyst composition comprises a metal phosphate of Formula (II) where a is 1, b is 0, c is 0, and d is 0. In one embodiment, the catalyst composition comprises a metal phosphate of Formula (II) where a is 0, b is 1, c is 0, and d is 0. In one embodiment, the catalyst composition comprises a metal phosphate of Formula (II) where a is 0, b is 0, c is 1, and d is 0. In one embodiment, the catalyst composition comprises a metal phosphate of Formula (II) where a is 0, b is 0, c is 0, and d is 1.

In one embodiment, the catalyst composition comprises a metal phosphate of Formula (II) wherein a is any number between 0 and 1 inclusive; b is any number between 0 and 1 inclusive; c is 0; and d is 0. In one embodiment, the catalyst composition comprises a metal phosphate of Formula (II) wherein a is any number between 0 and 1 inclusive; b is 0; c is any number between 0 and 1 inclusive; and d is 0. In one embodiment, the catalyst composition comprises a metal phosphate of Formula (II) wherein a is any number between 0 and 1 inclusive; b is 0; c is 0; and d is any number between 0 and 1 inclusive. In one embodiment, the catalyst composition comprises a metal phosphate of Formula (II) wherein a is 0; b is any number between 0 and 1 inclusive; c is any number between 0 and 1 inclusive; and d is 0. In one embodiment, the catalyst composition comprises a metal phosphate of Formula (II) a is 0; b is any number between 0 and 1 inclusive; c is 0; and d is any number between 0 and 1 inclusive. In one embodiment, the catalyst composition comprises a metal phosphate of Formula (II) wherein a is 0; b is 0; c is any number between 0 and 1 inclusive; and d is any number between 0 and 1 inclusive.

The catalyst composition may optionally further comprise at least one metal or metal ion selected from the lanthanides, the alkali metals, and the transition metals. In one embodiment, the catalyst composition may further comprise at least one metal or metal ion selected from the group consisting of Li, Na, K, Rb, Cs, Sc, Y, Lu, Ti, V, Cr, Mn, Fe, Co, Ni, Cu, Zn, Zr, Nb, Mo, Ru, Rh, Pd, Ag, Hf, Ta, W, Re, Os, Ir, Pt, Au, La, Ce, Pr, Nd, Sm, Eu, Gd, Tb, Dy, Ho, Er, Tm, and Yb. In one embodiment, the catalyst composition may further comprise at least one metal or metal ion selected from the group consisting of Li, Na, K, Rb, Cs, Sc, Y, Lu, Ti, V, Cr, Mn, Fe, Co, Ni, Cu, Zn, Zr, Nb, Mo, Ru, Rh, Pd, Ag, Ta, W, Re, Ir, Pt, Au, La, Ce, and Yb. In one embodiment, the optional metal(s) or metal ion(s) may be present in an amount less than about 50 mole percent of the total metals $[M_w+M'_x+M''_y+M'''_z]$. In one embodiment, the optional metal(s) or metal ion(s) may be present in an amount less than about 30 mole percent of the total metals $[M_w+M'_x+M''_y+M'''_z]$. In one embodiment, the optional metal(s) may be present in an amount less than about 15 mole percent of the total metals $[M_w+M'_x+M''_y+M'''_z]$. The optional metal(s) or metal ion(s) may be incorporated into the bulk hydroxyapatite during its synthesis, or may be added to the surface of the catalyst composition by methods known in the art.

The catalyst composition may further comprise at least one anionic additive selected from the group consisting of carbonate, silicate, aluminate, arsenate, vanadate, sulfate, and borate. Other additives may be used so long as the presence of the additive is not deleterious to the catalyst composition or its use in the process. In one embodiment, the additive may be present in an amount less than about 10 mole percent of the total metals $[M_w+M'_x+M''_y+M'''_z]$. In one embodiment, at least some of the phosphate groups of the hydroxyapatite may be substituted by one or more of these anionic additives, for example by arsenate or vanadate.

Catalyst compositions comprising a hydroxyapatite of Formula (I) can be obtained as nanocrystalline solids. The particles in the nanocrystalline catalyst composition can have dimensions which range from about 10 nm to about 50 nm in length in the shortest dimension and about 50 nm to about 500 nm in length in the longest dimension, for example from about 10 nm to about 50 nm in length in the shortest dimension and about 80 nm to about 400 nm in length in the longest dimension. Nanocrystalline catalysts can be advantageous due to their higher surface area which increases the amount of conversion per unit mass of catalyst.

The catalyst compositions can have surface areas of greater than about 2 meters squared per gram. In one embodiment, the catalyst compositions can have a surface area greater than about 5 meters squared per gram. In one embodiment, the catalyst compositions can have a surface area greater than about 10 meters squared per gram. Higher surface area is generally desirable for catalyst compositions as higher surface area can provide higher catalytic activity on a constant weight basis.

The catalyst composition comprising a hydroxyapatite of Formula (I) can be synthesized by the following methods. In one method, an aqueous salt solution containing one or more divalent metals selected from the group consisting of magnesium, calcium, strontium, and barium is prepared. The molar ratio of the divalent metals is selected to satisfy the stoichiometry of the hydroxyapatite of Formula (I). Preferred salts are metal nitrates, metal sulfates, and metal carboxylates. Most preferred are metal carboxylates. To the stirred aqueous metal salt solution are simultaneously added concentrated ammonium hydroxide (neat or as an about 5 M to about 15 M solution) and concentrated phosphoric acid (neat or as an about 2 M to about 15 M solution). The reagents can be added dropwise, or via a liquid pump at a rate of from about 1 to 10 mL/min, preferably from about 1 to 6 mL/min. The rates of ammonium hydroxide and phosphoric acid addition are adjusted to maintain a pH greater than about 10 in the reaction volume during addition. Temperatures during synthesis of the catalyst composition can be from about 0° C. to about 250° C. If necessary, suitable pressure equipment can be used. Agitation of the reaction medium can be accomplished with a magnetic stirring bar, or overhead mechanical stirrer. After completion of addition, the reaction can be stirred for a period of time from about 0.5 h to about 24 h, for example from about 1 h to 4 h. The solid that precipitates can be isolated by centrifugation or filtration. The solids can be optionally washed with water after isolation. After drying to remove water, the solid can be calcined at from about 400 to 800° C., preferably from 500 to 700° C., for a period of time from about 1 h to 24 h, for example about 2 h to about 15 h, or for example from about 2 h to 10 h, in an oven in air.

Alternatively, an aqueous metal hydroxide or metal oxide solution or slurry containing one or more divalent metals selected from the group consisting of magnesium, calcium, strontium, and barium is prepared. The molar ratio of the divalent metals is selected to satisfy the stoichiometry of the hydroxyapatite of Formula (I). To the stirred aqueous metal hydroxide solution (from about 0.02 to 3 M, preferably from 0.4 to 2.2 M) is added concentrated phosphoric acid (neat or as an about 0.1 M to about 15 M solution). Phosphoric acid can be added dropwise, or via a liquid pump at a rate of from about 1 to 10 mL/min, preferably from about 1 to 6 mL/min.

The pH of the reaction mixture is maintained at >10, preferably >12 during the addition of phosphoric acid. Excess metal hydroxide can be maintained in solution at the end of the reaction. Temperatures during synthesis of the catalyst composition can be from about 0° C. to about 250° C. If necessary, suitable pressure equipment can be used. Agitation of the reaction medium can be accomplished with a magnetic stirring bar, or overhead mechanical stirrer. After completion of addition, the reaction can be stirred for a period of time from about 0.5 h to 24 h, for example from about 1 h to 4 h. The solid that precipitates can be isolated by centrifugation or filtration. The solids can be optionally washed with water after isolation. After drying to remove water, the solid can be calcined at from about 400 to 800° C., preferably from 500 to 700° C., for a period of time from about 1 h to 24 h, for example about 2 h to 15 h, or for example 2 h to 10 h, in an oven in air.

Other synthetic methods known to those of skill in the art may also be used to prepare the catalyst compositions.

Metal phosphates of Formula (II) may be generated during the calcination procedures as an admixture with a hydroxyapatite of Formula (I). The presence of metal phosphates can be determined by X-ray powder diffraction analysis of the catalyst composition. In one embodiment, the catalyst composition may comprise from about 0 weight percent to about 25 weight percent metal phosphate. The amount of metal phosphate may optionally be greater than 25 weight percent.

Optionally, at least one metal or metal ion selected from the lanthanides, the alkali metals, and the transition metals can be added to the catalyst composition during the synthesis procedure. The metal or metal ion may be added, for example, by reacting or physically mixing the catalyst composition with metals, metal compounds, or metal salts before or after the calcination procedure. Alternatively, the catalyst composition may be reacted with metal compounds or salts in appropriate solvents, before or after the calcination procedure. At least one additive selected from the group consisting of carbonate, silicate, aluminate, arsenate, vanadate, sulfate, and borate may be added to the catalyst composition in a similar manner. The optional metal(s) and/or additive may be incorporated into the bulk hydroxyapatite during its synthesis, or may be added to the surface of the initial catalyst composition.

Preparation of the catalyst composition for use in a process to produce 2-ethylhexanol can further include pelletizing the solid catalyst composition, crushing and sieving the material, and optionally calcining the material at a temperature from about 400 to 800° C., preferably from 500 to 700° C., for a period of time from about 1 h to 24 h, for example about 2 h to 15 h, or for example 2 to 10 h, in an oven in air.

Base-Treated Catalyst Composition:

Base treatment of a catalyst composition comprising a hydroxyapatite of Formula (I) as described herein above or a hydroxyapatite of Formula (III) as described herein below is expected to provide a catalyst composition having better performance for producing 2-ethylhexanol, for example a catalyst composition providing higher activity and/or higher selectivity to 2-ethylhexanol.

In one embodiment of the process to produce a reaction product comprising 2-ethylhexanol, the catalyst composition comprises a base-treated catalyst composition obtained by contacting an initial catalyst composition comprising a hydroxyapatite of Formula (I) with a base. The initial catalyst composition comprises at least one hydroxyapatite based on unary, binary, tertiary, and quaternary combinations of magnesium, calcium, strontium, and barium cations. The catalyst composition comprises a hydroxyapatite of Formula (I).

In one embodiment, the catalyst composition comprises a hydroxyapatite of Formula (I) wherein w is 1, x is 0, y is 0, and z is 0. In one embodiment, the catalyst composition comprises a hydroxyapatite of Formula (I) wherein w is 0, x is 0, y is 1, and z is 0. In one embodiment, the catalyst composition comprises a hydroxyapatite of Formula (I) wherein w is 0, x is 0, y is 0, and z is 1.

In one embodiment, the catalyst composition comprises a hydroxyapatite of Formula (I) wherein w is any number between 0 and 1 inclusive; x is any number from 0 to less than 0.5; y is 0; and z is 0. In one embodiment, the catalyst composition comprises a hydroxyapatite of Formula (I) wherein w is any number between 0 and 1 inclusive; x is 0; y is any number between 0 and 1 inclusive; and z is 0. In one embodiment, the catalyst composition comprises a hydroxyapatite of Formula (I) wherein w is any number between 0 and 1 inclusive; x is 0; y is 0; and z is any number between 0 and 1 inclusive. In one embodiment, the catalyst composition comprises a hydroxyapatite of Formula (I) wherein w is 0; x is any number from 0 to less than 0.5; y is any number between 0 and 1 inclusive; and z is 0. In one embodiment, the catalyst composition comprises a hydroxyapatite of Formula (I) w is 0; x is any number from 0 to less than 0.5; y is 0; and z is any number between 0 and 1 inclusive. In one embodiment, the catalyst composition comprises a hydroxyapatite of Formula (I) wherein w is 0; x is 0; y is any number between 0 and 1 inclusive; and z is any number between 0 and 1 inclusive.

In another embodiment of the process to produce a reaction product comprising 2-ethylhexanol, the catalyst composition comprises a base-treated catalyst composition obtained by contacting an initial catalyst composition comprising a hydroxyapatite of Formula (III) with a base.

The initial catalyst composition comprises at least one hydroxyapatite based on unary, binary, tertiary, and quaternary combinations of magnesium, calcium, strontium, and barium cations. The initial catalyst composition comprises a hydroxyapatite of Formula (III):

$$(M_m M'_n M''_p M'''_q)_5(PO_4)_3(OH) \quad \text{(III)}$$

where
M is Mg;
M' is Ca;
M'' is Sr;
M''' is Ba;
m is any number between 0 and 1 inclusive;
n is any number between 0 and 1 inclusive;
p is any number between 0 and 1 inclusive;
q is any number between 0 and 1 inclusive;
and m+n+p+q=1.

With respect to M, M', M'', and M''', each of the metals is optional in the catalyst composition to the extent that at least one of the metals has to be present to conform to the above formulation.

In one embodiment, the initial catalyst composition comprises a hydroxyapatite of Formula (III) where m is 1, n is 0, p is 0, and q is 0. In one embodiment, the initial catalyst composition comprises a hydroxyapatite of Formula (III) where m is 0, n is 1, p is 0, and q is 0. In one embodiment, the initial catalyst composition comprises a hydroxyapatite of Formula (III) where m is 0, n is 0, p is 1, and q is 0. In one embodiment, the initial catalyst composition comprises a hydroxyapatite of Formula (III) where m is 0, n is 0, p is 0, and q is 1.

In one embodiment, the initial catalyst composition comprises a hydroxyapatite of Formula (III) wherein m is any number between 0 and 1 inclusive; n is any number between 0 and 1 inclusive; p is 0; and q is 0. In one embodiment, the initial catalyst composition comprises a hydroxyapatite of Formula (III) wherein m is any number between 0 and 1 inclusive; n is 0; p is any number between 0 and 1 inclusive; and q is 0. In one embodiment, the initial catalyst composition comprises a hydroxyapatite of Formula (III) wherein m is any number between 0 and 1 inclusive; n is 0; p is 0; and q is any number between 0 and 1 inclusive. In one embodiment, the initial catalyst composition comprises a hydroxyapatite of Formula (III) wherein m is 0; n is any number between 0 and 1 inclusive; p is any number between 0 and 1 inclusive; and q is 0. In one embodiment, the initial catalyst composition comprises a hydroxyapatite of Formula (III) m is 0; n is any number between 0 and 1 inclusive; p is 0; and q is any number between 0 and 1 inclusive. In one embodiment, the initial catalyst composition comprises a hydroxyapatite of Formula (III) wherein m is 0; n is 0; p is any number between 0 and 1 inclusive; and q is any number between 0 and 1 inclusive.

The initial catalyst composition comprising a hydroxyapatite of Formula (I) or Formula (III) may optionally further comprise at least one metal phosphate of Formula (II).

The metal phosphate may comprise, for example, Mg, Ca, Sr, and Ba, or any three of these elements, or any two of these elements, or only one of these elements. In one embodiment, the initial catalyst composition comprises a metal phosphate of Formula (II) where a is 1, b is 0, c is 0, and d is 0. In one embodiment, the initial catalyst composition comprises a metal phosphate of Formula (II) where a is 0, b is 1, c is 0, and d is 0. In one embodiment, the initial catalyst composition comprises a metal phosphate of Formula (II) where a is 0, b is 0, c is 1, and d is 0. In one embodiment, the initial catalyst composition comprises a metal phosphate of Formula (II) where a is 0, b is 0, c is 0, and d is 1.

In one embodiment, the initial catalyst composition comprises a metal phosphate of Formula (II) wherein a is any number between 0 and 1 inclusive; b is any number between 0 and 1 inclusive; c is 0; and d is 0. In one embodiment, the initial catalyst composition comprises a metal phosphate of Formula (II) wherein a is any number between 0 and 1 inclusive; b is 0; c is any number between 0 and 1 inclusive; and d is 0. In one embodiment, the initial catalyst composition comprises a metal phosphate of Formula (II) wherein a is any number between 0 and 1 inclusive; b is 0; c is 0; and d is any number between 0 and 1 inclusive. In one embodiment, the initial catalyst composition comprises a metal phosphate of Formula (II) wherein a is 0; b is any number between 0 and 1 inclusive; c is any number between 0 and 1 inclusive; and d is 0. In one embodiment, the initial catalyst composition comprises a metal phosphate of Formula (II) a is 0; b is any number between 0 and 1 inclusive; c is 0; and d is any number between 0 and 1 inclusive. In one embodiment, the initial catalyst composition comprises a metal phosphate of Formula (II) wherein a is 0; b is 0; c is any number between 0 and 1 inclusive; and d is any number between 0 and 1 inclusive.

The initial catalyst composition may optionally further comprise at least one metal or metal ion selected from the lanthanides, the alkali metals, and the transition metals. In one embodiment, the initial catalyst composition may further comprise at least one metal or metal ion selected from the group consisting of Li, Na, K, Rb, Cs, Sc, Y, Lu, Ti, V, Cr, Mn, Fe, Co, Ni, Cu, Zn, Zr, Nb, Mo, Ru, Rh, Pd, Ag, Hf, Ta, W, Re, Os, Ir, Pt, Au, La, Ce, Pr, Nd, Sm, Eu, Gd, Tb, Dy, Ho, Er, Tm, and Yb. In one embodiment, the initial catalyst composition may further comprise at least one metal or metal ion selected from the group consisting of Li, Na, K, Rb, Cs, Sc, Y, Lu, Ti, V, Cr, Mn, Fe, Co, Ni, Cu, Zn, Zr, Nb, Mo, Ru, Rh, Pd, Ag, Ta, W, Re, Ir, Pt, Au, La, Ce, and Yb. In one embodiment, the optional metal(s) or metal ion(s) may be present in an amount less than about 50 mole percent of the total metals $[M_w+M'_x+M''_y+M'''_z]$ or $[M_m+M'_n+M''_p+M'''_q]$. In one embodiment, the optional metal(s) or metal ion(s) may be present in an amount less than about 30 mole percent of the total metals $[M_w+M'_x+M''_y+M'''_z]$ or $[M_m+M'_n+M''_p+M'''_q]$. In one embodiment, the optional metal(s) or metal ion(s) may be present in an amount less than about 15 mole percent of the total metals $[M_w+M'_x+M''_y+M'''_z]$ or $[M_m+M'_n+M''_p+M'''_q]$. The optional metal(s) or metal ion(s) may be incorporated into the bulk hydroxyapatite during its synthesis, or may be added to the surface of the initial catalyst composition.

The initial catalyst composition may further comprise at least one anionic additive selected from the group consisting of carbonate, silicate, aluminate, arsenate, vanadate, sulfate, and borate. Other additives may be used so long as the presence of the additive is not deleterious to the catalyst composition or its use in the process. In one embodiment, the additive may be present in an amount less than about 10 mole percent of the total metals $[M_w+M'_x+M''_y+M'''_z]$ or $[M_m+M'_n+M''_p+M'''_q]$. In one embodiment, at least some of the phosphate groups of the hydroxyapatite may be substituted by one or more of these anionic additives, for example by arsenate or vanadate.

Base-treated catalyst compositions derived from a hydroxyapatite of Formula (I) or Formula (III) can be obtained as nanocrystalline solids. The particles in the nanocrystalline base-treated catalyst composition can have dimensions which range from about 10 nm to about 50 nm in length in the shortest dimension and about 50 nm to about 500 nm in length in the longest dimension, for example from about 10 nm to about 50 nm in length in the shortest dimension and about 80 nm to about 400 nm in length in the longest dimension. Nanocrystalline catalysts can be advantageous due to their higher surface area which increases the amount of conversion per unit mass of catalyst.

The base-treated catalyst compositions can have surface areas of greater than about 2 meters squared per gram. In one embodiment, the catalyst compositions can have a surface area greater than about 5 meters squared per gram. In one embodiment, the catalyst compositions can have a surface area greater than about 10 meters squared per gram. Higher surface area is generally desirable for catalyst compositions as higher surface area can provide higher catalytic activity on a constant weight basis.

The initial catalyst composition comprising a hydroxyapatite of Formula (III) can be synthesized by the methods described above for a catalyst composition comprising a hydroxyapatite of Formula (I), except that the molar ratio of the divalent metals is selected to satisfy the stoichiometry of the hydroxyapatite of Formula (III).

Preferably, the initial catalyst composition comprising a hydroxyapatite of Formula (I) or Formula (III) is calcined before treatment with base.

The initial catalyst composition is contacted with a base to produce a base-treated catalyst composition useful in the process of producing a reaction product comprising 2-ethylhexanol. In one embodiment, the base comprises an aqueous solution of a metal hydroxide $Q(OH)_f$ where f is 1 to 3 inclusive and Q is at least one metal selected from the group consisting of Li, Na, K, Rb, Cs, Sc, Y, Lu, Ti, V, Cr, Mn, Fe, Co, Ni, Cu, Zn, Zr, Nb, Mo, Ru, Rh, Pd, Ag, Hf, Ta, W, Re, Os, Ir, Pt, Au, La, Ce, Pr, Nd, Sm, Eu, Gd, Tb, Dy, Ho, Er, Tm, and Yb. In one embodiment, Q is at least one metal selected from the group consisting of Li, Na, K, Rb, Cs, Sc, Y, Lu, Ti, V, Cr, Mn, Fe, Co, Ni, Cu, Zn, Zr, Nb, Mo, Ru, Rh, Pd, Ag, Ta, W, Re, Ir, Pt, Au, La, Ce, and Yb. In one embodiment, Q is at least one metal selected from the group consisting of Mg, Ca, Sr, and Ba. The metal hydroxide $Q(OH)_f$ can be obtained commercially or can be generated by adding the corresponding metal oxide to water. The pH of the aqueous solution of the metal hydroxide $Q(OH)_f$ should be greater than about 11, for example greater than about 12, or for example greater than about 12.5. The aqueous solution may contain organic solvents as long as the presence of the organic solvent is not deleterious to the process of treating with a base or to the base-treated catalyst composition.

The base-treated catalyst composition can be isolated by filtration or centrifugation. After isolation, the base-treated catalyst composition can be washed with water. In one embodiment, the base-treated catalyst composition is washed with a total of about 0 to about 20 mL of water per g of solid isolated. In one embodiment, the base-treated catalyst composition is washed with about 0 to about 11 mL of water per g of solid. The use of a minimal amount of water, such as less than about 11 mL of water per gram of isolated solid to wash the isolated base-treated catalyst composition can provide improved selectivity to alcohols in a process for producing a reaction product comprising 2-ethylhexanol from a reactant comprising 1-butanol. Optionally, the base-treated catalyst can be dried to remove water.

Preparation of the catalyst composition for use in a process to produce 2-ethylhexanol can further include pelletizing the solid base-treated catalyst composition, crushing and sieving the material, and optionally calcining the material at a temperature from about 400 to 800° C., preferably from 500 to 700° C., for a time of about 1 to 24 h, preferably 2 to 10 h in an oven in air.

Contacting the initial catalyst composition with base may be performed in a stirred, or otherwise agitated, batch reactor. The base treatment may be done in air or under an inert atmosphere, such as nitrogen or argon. Optionally, the amount of carbon dioxide present is minimized to reduce its reaction with the base.

Contacting the initial catalyst composition with base is carried out under suitable treatment conditions including a treatment temperature of about 30° C. to about 300° C. In another embodiment, contacting the initial catalyst composition with base is carried out at a temperature of about 25° C. to about 300° C., for example about 30° C. to about 200° C. In another embodiment, contacting the initial catalyst composition with base is carried out at a temperature of about 50° C. to about 200° C.

Contacting the initial catalyst composition with base is carried out for a treatment time of about 1 minute to about 24 hours. Longer periods of base treatment, such as several days, are possible, however a shorter period of time may be preferable for practical, economic reasons. In one embodiment, contacting the initial catalyst composition with base is carried out for a treatment time of about 1 minute to about 18 hours.

In one embodiment, contacting the initial catalyst composition with base may be performed at a relatively high temperature for a relatively short period of time, for example at about 150° C. to about 300° C. for about 1 minute to about 12 hours. In another embodiment, contacting the initial catalyst composition with base may be performed at a lower temperature for a relatively long period of time, for example from about 30° C. to about 150° C. for about 1 to about 48 hours. In one embodiment, contacting the initial catalyst composition with base at about 100° C. is carried out for a treatment time of about 45 minutes to about 90 minutes. Other temperature and treatment time combinations intermediate to these may also be used.

For the process of contacting the initial catalyst composition with base, the temperature, treatment time, pH, metal hydroxide used, initial catalyst composition, and particle size of the initial catalyst composition are related; thus these variables may be adjusted as necessary for each type of initial catalyst composition to optimize the base treatment processes described herein.

Process for Treating Initial Catalyst Composition with Base:

In one process to produce a base-treated catalyst composition, the process comprises contacting an initial catalyst composition comprising a hydroxyapatite of Formula (I) with a base at a temperature from about 30° C. to about 300° C. and for a time of about 1 minute to about 24 hours to produce a base-treated catalyst composition.

In another process to produce a base-treated catalyst composition, the process comprises contacting an initial catalyst composition comprising a hydroxyapatite of Formula (III) with a base at a temperature from about 30° C. to about 300° C. and for a time of about 1 minute to about 24 hours to produce a base-treated catalyst composition.

The initial catalyst composition of either process can be obtained as described above herein, and can further comprise a metal phosphate; at least one metal or metal ion selected from the lanthanides, the alkali metals, and the transition metals; at least one additive selected from the group consisting of carbonate, silicate, aluminate, arsenate, vanadate, sulfate, and borate; as described above herein. The base can be as described above herein. The method of contacting the initial catalyst composition and the base can be as described above herein. The process may further comprise the step of washing the base-treated catalyst composition with a minimal amount of water. The washing step may be done at ambient temperature.

A composition comprising a base-treated catalyst derived from a hydroxyapatite of the Formula $(M_wM'_xM''_yM'''_z)_5(PO_4)_3(OH)$ wherein M is Mg; M' is Ca; M" is Sr; M''' is Ba; w is any number between 0 and 1 inclusive; x is any number from 0 to less than 0.5; y is any number between 0 and 1 inclusive; z is any number between 0 and 1 inclusive; and w+x+y+z=1; is obtained by the process of contacting an initial catalyst composition comprising a hydroxyapatite of Formula (I) with base as described above herein.

A composition comprising a base-treated catalyst derived from a hydroxyapatite of the Formula $(M_mM'_nM''_pM'''_q)_5(PO_4)_3(OH)$ wherein M is Mg; M' is Ca; M" is Sr; M''' is Ba; m is any number between 0 and 1 inclusive; n is any number between 0 and 1 inclusive; p is any number between 0 and 1 inclusive; q is any number between 0 and 1 inclusive; and m+n+p+q=1; is obtained by the process of contacting an initial catalyst composition comprising a hydroxyapatite of Formula (III) with base as described above herein.

Process to Produce a Reaction Product Comprising 2-Ethylhexanol:

In one embodiment of the invention, a process is provided in which a gas phase reactant stream comprising 1-butanol is contacted with a catalyst composition as described herein at a temperature and pressure sufficient to produce a reaction product comprising 2-ethylhexanol. The gas phase reactant stream may be anhydrous, for example containing less than about 0.1 weight percent water, or may contain some water, for example up to about 10 wt % water). The gas phase reactant stream may further comprise other alcohols, such as methanol, ethanol, other butanol isomers, higher alcohols, and mixtures thereof. Optionally, the gas phase reactant stream may contain an inert gas such as nitrogen, carbon dioxide, or a mixture thereof. The reaction product further comprises water and unreacted 1-butanol, if 1-butanol conversion is less than complete. The reaction product may further comprise alcohols containing more than six carbon atoms and other organic species such as alkenes, alkanes, ethers, aldehydes, and esters. Suitable temperatures for the catalytic conversion of a reactant comprising 1-butanol to a reaction product comprising 2-ethylhexanol are in the range of about 150° C. to about 500° C., for example about 200° C. to about 500° C., or about 350° C. to about 425° C. Suitable pressures are from about 0.1 MPa to about 20.7 MPa. Suitable contact times on the catalyst can range from about 0.25 seconds to about 25 seconds.

The reactant stream comprising 1-butanol can be obtained from any convenient source. For example, 1-butanol may be obtained synthetically by Guerbet synthesis from ethanol using the catalyst compositions disclosed herein. The reactant stream comprising 1-butanol may also be obtained by fermentation. For example, 1-butanol may be produced fermentatively by microbial hosts selected from bacteria, cyanobacteria, filamentous fungi, and yeasts, as disclosed for example in U.S. patent application Ser. No. 12/758,870 filed on Apr. 13, 2010, using sugars, optionally obtained from cellulosic materials as the carbon and energy source for growth. The microbial host used should be tolerant to the butanol product produced, so that the yield is not limited by toxicity of the product to the host. Suitable microbial hosts for the production of butanol include, but are not limited to, members of the genera, *Zymomonas, Escherichia, Salmonella, Rhodococcus, Pseudomonas, Bacillus, Lactobacillus, Enterococcus, Pediococcus, Alcaligenes, Klebsiella, Paenibacillus, Arthrobacter, Corynebacterium, Brevibacterium, Pichia, Issatchenkia, Candida, Hansenula* and *Saccharomyces*. Preferred hosts include: *Escherichia coli, Alcaligenes eutrophus, Bacillus licheniformis, Paenibacillus macerans, Rhodococcus erythropolis, Pseudomonas putida, Lactobacillus plantarum, Enterococcus faecium, Enterococcus gallinarum, Enterococcus faecalis, Pediococcus pentosaceus, Pediococcus acidilactici, Bacillus subtilis* and *Saccharomyces cerevisiae*.

Microorganisms mentioned above may be genetically modified to convert fermentable carbon sources into butanol, specifically 1-butanol, 2-butanol, or isobutanol, using methods known in the art. Particularly suitable microorganisms include *Escherichia, Lactobacillus*, and *Saccharomyces*, where *E. coli, L. plantarum* and *S. cerevisiae* are particularly preferred. Additionally, the microorganism may be a butanol-tolerant strain of one of the microorganisms listed above that is isolated using the method described by Bramucci et al. in U.S. Pat. No. 7,541,173.

The result of the fermentation is a fermentation broth, from which the 1-butanol may be extracted with an appropriate solvent to produce a stream comprising the extractant, water, and 1-butanol, for example as disclosed in U.S. Published Patent Application No. 2009/0305370 and U.S. patent application Ser. No. 12/758,870 filed on Apr. 13, 2010. The butanol-containing stream may then be refined using distillation to obtain 1-butanol, for example as disclosed in WO 2011/008924 and WO 2011/008927. The butanol can be used as the reactant stream for the present invention, or one or more drying procedures can be performed to reduce the amount of water in the stream before its use. For example, the wet 1-butanol stream may be passed over a desiccant, such as molecular sieves, until the desired amount of water has been removed.

The catalyst compositions useful in the process to produce a reaction product comprising 2-ethylhexanol can be catalyst compositions comprising a hydroxyapatite of Formula (I) or base-treated catalyst compositions obtained by treating an initial catalyst composition comprising a hydroxyapatite of Formula (I) or Formula (III) with a base, as described above herein. The catalyst compositions may be prepared as described above herein. The catalyst compositions may be used in the form of powders, granules, spheres, pellets, or other particulate forms. Selection of an optimal average particle size for the catalyst composition will depend upon such process parameters as reactor residence time and desired reactor flow rates.

The catalytic conversion of 1-butanol to the reaction product can be run in either batch or continuous mode as described, for example, in H. Scott Fogler, (*Elements of Chemical Reaction Engineering*, $2^{nd}$ Edition, (1992) Prentice-Hall Inc, CA). Suitable reactors include fixed-bed, adiabatic, fluid-bed, transport bed, and moving bed.

The catalyst composition may be treated with nitrogen or air at elevated temperatures prior to its use. One protocol that has been found to be effective is described in more detail in Example 1, below. If the catalyst composition comprises at least one transition metal, the catalyst composition may be treated with hydrogen at elevated temperatures prior to its use. If catalyst treatment is desired, the catalyst may be treated in situ in the reactor or ex situ and then introduced into the reactor.

During the course of the reaction, the catalyst may become fouled, and, therefore, it may be necessary to regenerate the catalyst. Preferred methods of catalyst regeneration include, contacting the catalyst composition with a gas such as, but not limited to, air, steam, hydrogen, nitrogen or combinations thereof, at an elevated temperature, although care must be taken not to use a temperature that is so high that the regeneration results in a loss of surface area or other unwanted effects. If catalyst regeneration is desired, the catalyst may be regenerated in situ in the reactor or ex situ and then introduced into the reactor.

One skilled in the art will know that conditions, such as temperature, pressure, catalyst composition, reactor configuration and contact time can affect the reaction kinetics, product yield and product selectivity. Standard experimentation can be used to optimize the yield of 2-ethylhexanol from the reaction.

2-Ethylhexanol can be separated from the reaction product by known chemical engineering methods, including distillation. Other specific chemicals (or combinations of chemicals) also can be removed from the reaction product using known chemical engineering methods. The specific methods will be dependent on the nature of the reaction product, which, in turn, is dependent on the specific catalyst used and the reaction conditions, particularly the extent of 1-butanol conversion.

Advantages of the Present Methods:

The processes disclosed herein for producing 2-ethylhexanol from a reactant comprising 1-butanol use catalyst compositions which offer long catalyst lifetime, good selectivity to 2-ethylhexanol, and low production of alkenes, aldehydes, esters, and ethers. Further advantages include the use of a vapor phase process in which separation of the solid catalyst from the gaseous product is simple and economical, and the use of catalyst compositions which can easily be regenerated, if necessary. Additionally, the use of catalyst compositions which do not require base addition during the production of 2-ethylhexanol can simplify the process and provide improved economics.

The processes to produce a reaction product comprising 2-ethylhexanol disclosed herein, the catalyst compositions disclosed herein, and the 2-ethylhexanol produced by the processes disclosed herein, may be used in a process for making a dialkyl ether composition comprising two or more ethers, as disclosed for example in published patent application WO2009/064828. Such dialkyl ether compositions are useful as a fuel additive.

EXAMPLES

The present invention is further defined in the following examples. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various uses and conditions.

The following materials were used in the examples. All commercial reagents were used as received. 1-Butanol (99%) was obtained from Sigma-Aldrich, St. Louis, Mo. Strontium acetate (99.99%), strontium hydroxide (95%), and phosphoric acid (99.99%) were obtained from Sigma Aldrich (Milwaukee, Wis.). Ammonium hydroxide (>99%) was obtained from EMD Chemicals, Gibbstown, N.J.

Electron Spectroscopy for Chemical Analysis (ESCA) was performed using a Quantera SXM (Scanning X-ray Photoelectron Spectroscopy Microprobe) (ULVAC-PHI, Inc.) using the following X-ray settings: 100 μm, 100 W, 17.5 kV, monochromatic Aluminum X-rays. An analysis area of 1350 μm×200 μm was examined. High resolution detail spectral acquisition was achieved using 55 eV pass energy with a 0.2 eV step size.

Powder X-ray diffraction was used for the identification of crystalline phases. Data were obtained with a Philips X'PERT automated powder diffractometer, Model 3040. The diffractometer was equipped with automatic variable anti-scatter and divergence slits, X'Celerator RTMS detector, and Ni filter. The radiation was CuKα (45 kV, 40 mA). Data were collected at room temperature from 4 to 60 degrees 2-theta; using a continuous scan with an equivalent step size of 0.02 deg; and a count time of 80 seconds per step in theta-theta geometry. The sample was ground with an agate mortar and pestle and smeared on an amorphous silicon sample holder. A few drops of collodion were applied to secure the powder sample on the holder. MDI/Jade software was used with the International Committee for Diffraction Data database for phase identification.

Elemental analyses were performed by inductively coupled atomic emission spectroscopy (ICP-AES) using a Perkin Elmer, Model=Optima 5300 instrument used in radial view mode. Analyses were also done on an ELEMENT-2 High Resolution Inductively Coupled Plasma Mass Spectrometer (HR-ICP-MS) manufactured by Thermo Scientific, Inc., and on an Agilent 7500ce ICP-MS.

A Tecnai F-20 Scanning Transmission Electron Microscope (TEM) equipped with a field-emitting electron source was used for the structural and compositional identification of the catalysts. The microscope was operated at an accelerating voltage of 200 kV. The microscope was also equipped with an Oxford Instruments INCA x-sight energy dispersive spectroscopy (EDS) system to identify elements as light as Boron. The EDS system had a Li-doped Si detector and an ATW ultra-thin window. Samples were prepared by dry-dusting them onto holey-carbon coated copper TEM grids (3 mm diameter) without the use of any liquid dispersing aids. Images were acquired using a cold CCD camera mounted on the bottom of the TEM column.

BET surface area was determined using nitrogen adsorption/desorption measurements performed at 77.3° K. on a Micromeritics, Inc. ASAP model 2400/2405 porosimeter. Samples were degassed at 150° C. overnight prior to data collection. Surface area measurements utilized a five-point adsorption isotherm collected from 0.05 to 0.20 p/p₀ and analyzed via the BET method.

In the Tables, "Cony." means conversion, "BuOH" means 1-butanol, and "Sel." means selectivity. 1-Butanol conversion (%) was calculated as follows: [(1-carbon moles of unreacted 1-butanol)/carbon moles of total outlet gases] times 100. Total 2-ethylhexanol selectivity (%) was calculated as follows: (carbon moles of 2-ethylhexanol product/carbon moles of 1-butanol reacted) times 100.

Example

Three batches of nanocrystalline $Sr_{10}(PO_4)_6(OH)_2$ were prepared and separately treated with $Sr(OH)_2$ to provide base-treated catalyst compositions comprising a strontium hydroxyapatite. The base-treated catalyst compositions were combined as described below and used to produce a product comprising 2-ethylhexanol from 1-butanol under three different reaction conditions.

Synthesis of Base-Treated Catalyst Compositions:

A first batch of material was prepared as follows: A three-necked round-bottomed flask equipped with a pH probe and two inlets for syringe pump tubing was charged with 28.12 g of strontium acetate dissolved in 250.0 mL of deionized water. To this was added via syringe pump 15.58 mL of a 5.24 M solution of phosphoric acid at a rate of 1.039 mL/min. Simultaneously, a concentrated ammonium hydroxide solution (14.5 M) was added via another syringe pump at a rate of 5.000 mL/min maintaining a pH of >10.0 in the round-bottomed flask during the addition of the reagents. The mixture was stirred vigorously during addition, and for 2 h following completion of addition. The above procedures were done at ambient room temperature.

The white precipitate that formed was isolated by filtration, was washed twice with 100 mL portions of deionized water, and was dried in a vacuum oven overnight at 100° C. Yield of dry product, the initial catalyst composition, was 19.97 g. X-ray powder diffraction of this product showed the presence of a crystalline compound identified as primarily $Sr_{10}(PO_4)_6(OH)_2$. BET Surface Area: 62.4 m²/g. Transmission Electron Microscopy (TEM) analysis showed the product was primarily $Sr_{10}(PO_4)_6(OH)_2$ rod-like nanocrystals with dimensions of from 10 to 40 nm along the short dimension to 50-300 nm in length. The material was calcined at 600° C. for 8 h in an oven.

To a 500 mL round-bottomed borosilicate flask was charged 6.00 g of the calcined initial catalyst composition and 63.25 mL of a saturated solution of strontium hydroxide (1.7 g of $Sr(OH)_2(H_2O)_8$/100 mL). This was refluxed under nitrogen for one hour. After cooling the base-treated product was isolated by filtration, and then dried in a vacuum oven at 100° C. overnight yielding 6.38 g of base-treated catalyst composition as product.

X-ray powder diffraction of this product showed the presence of a crystalline compound identified as primarily $Sr_{10}(PO_4)_6(OH)_2$. BET Surface Area: 38.6 m²/g. TEM analysis showed the base-treated product was primarily $Sr_{10}(PO_4)_6(OH)_2$ rod-like nanocrystals with dimensions of from 10 to 40 nm along the small dimension to 50-300 nm in length.

A second batch of material was prepared in a similar manner to the procedure for the first batch, except that the material obtained after the step of base treatment with saturated strontium hydroxide was not washed with water, and was dried as obtained after isolating by filtration. X-ray powder diffraction of this product showed the presence of a crystalline compound identified as primarily $Sr_{10}(PO_4)_6(OH)_2$. BET Surface Area: 40.2 m²/g. TEM analysis showed the base-treated product was primarily $Sr_{10}(PO_4)_6(OH)_2$ rod-like nanocrystals with dimensions of from 10 to 40 nm along the small dimension to 50-300 nm in length.

A third batch of material was prepared in a similar manner to the procedure for the first batch, except in the base treatment step with saturated strontium hydroxide, and additional 0.2 g of strontium hydroxide per 5.00 grams of treated solid was added into the reaction flask, and the solid from the base treatment step was not washed with water after isolation by filtration. X-ray powder diffraction of this product showed the presence of a crystalline compound identified as primarily $Sr_{10}(PO_4)_6(OH)_2$. BET Surface Area: 38.6 m$^2$/g. TEM pictures showed the base-treated product was primarily $Sr_{10}(PO_4)_6(OH)_2$ rod-like nanocrystals with dimensions of from 10 to 40 nm along the small dimension to 50-300 nm in length.

Each of the three batches of base-treated catalyst compositions were separately pelletized in a Specac 1 inch stainless steel pellet die at 25,000 psi with a Preco hydraulic press (model number PA7-1), crushed with a mortar and pestle, and sieved through a 20 mesh screen onto a 40 mesh screen, allowing fines to be removed. The material was calcined via the following sequence: room temperature to 475° C. at 30° C./min rise; hold at 475° C. for 10 min; 475° C. to 525° C. at 5° C./min; hold at 525° C. for 10 min; 525° C. to 550° C. at 1° C./min; hold at 550° C. for 8 h. Cool 550° C. to 110° C. at <30° C./min; then allow to cool to room temperature.

Combination and Evaluation of Base-Treated Catalyst Compositions:

A portion of the first batch of base-treated catalyst composition (1.1475 g) was combined with 0.9630 g of the second batch, and 0.5873 g of the third batch of material. The combined catalyst composition was evaluated according to the following procedure.

Approximately 2.60 grams of the combined catalyst composition was loaded on a stainless steel mesh support within a 18 inch×½ inch (45.7 cm×1.3 cm) outside diameter type 316 stainless steel tube reactor with inlets for gas and liquid feeds. The catalyst composition was then pre-conditioned in situ in the reactor by flowing nitrogen gas at 15 mL/min, initially at room temperature, then raising the temperature to 400° C. and introducing the 1-butanol to generate reaction data. At reaction temperature nitrogen flow was set at 15 mL/min and 1-butanol flow at either 2 mL/h or 4 mL/h as shown in the Table below. After operating at 4 ml/hr the reactor was shut down for 3 days and then restarted with the reactor temperature lowered to 380° C. and a butanol flowrate of 2 mL/h.

The gaseous product stream was kept at 215° C. and fed directly to an Agilent™6890 GC equipped with flame ionization and mass selective detectors. Results are shown in the Table below. The results represent steady state data from the vapor phase butanol condensation reaction at 3 different process conditions and demonstrate the production of 2-ethylhexanol in good selectivity.

Although particular embodiments of the present invention have been described in the foregoing description, it will be understood by those skilled in the art that the invention is capable of numerous modifications, substitutions, and rearrangements without departing from the spirit of essential attributes of the invention. Reference should be made to the appended claims, rather than to the foregoing specification, as indicating the scope of the invention.

What is claimed is:

1. A process comprising the step of:
   contacting a reactant comprising 1-butanol with a base-treated catalyst composition under suitable reaction conditions to produce a reaction product comprising 2-ethylhexanol;
   wherein the suitable reaction conditions include a temperature of about 350° C. to about 425° C. and a pressure from about 0.1 MPa to about 20.7 MPa; and
   wherein the base-treated catalyst composition is obtained by treating an initial catalyst composition comprising a hydroxyapatite of Formula (III):

$$(M_m M'_n M''_p M'''_q)_5 (PO_4)_3 (OH) \qquad (III)$$

wherein
   M is Mg;
   M' is Ca;
   M" is Sr;
   M'" is Ba;
   m is any number between 0 and 1 inclusive;
   n is any number between 0 and 1 inclusive;
   p is any number between 0 and 1 inclusive;
   q is any number between 0 and 1 inclusive;
   and m+n+p+q=1 with a base at a treatment temperature from about 25° C. to about 300° C. for a treatment time of about 1 minute to about 24 hours, and optionally washing the isolated base-treated catalyst composition with a minimal amount of water.

2. A process comprising the step of:
   contacting a reactant comprising 1-butanol with a base-treated catalyst composition under suitable reaction conditions to produce a reaction product comprising 2-ethylhexanol;
   wherein the suitable reaction conditions include a temperature of about 350° C. to about 425° C. and a pressure from about 0.1 MPa to about 20.7 MPa; and
   wherein the base-treated catalyst composition is obtained by treating an initial catalyst composition comprising a hydroxyapatite of Formula (I):

$$(M_w M'_x M''_y M'''_z)_5 (PO_4)_3 (OH) \qquad (I)$$

wherein
   M is Mg;
   M' is Ca;
   M" is Sr;
   M'" is Ba;
   w is any number between 0 and 1 inclusive;

TABLE

| | | | | | | | | | | | |
|---|---|---|---|---|---|---|---|---|---|---|---|
| Temp (° C.) | 1-BuOH feedrate (mL/hr) | 1-BuOH (Conv %) | Butenes (% Sel) | 1-Butanal (% Sel) | 1,2-Dimethyl Cyclohexene (% Sel) | n-Butyl ether (% Sel) | 2-Ethyl hexanal (% Sel) | n-Butyl Butyrate (% Sel) | 2-Ethyl 2-Hexenal (% Sel) | 2-Ethyl-1-hexanol (% Sel) | 2-ethyl-2-Hexen-1-ol (% Sel) |
| 400 | 2 | 31.88 | 15.24 | 12.69 | 6.02 | 1.66 | 3.21 | 0.56 | 4.53 | 38.07 | 1.79 |
| 400 | 4 | 18.58 | 8.22 | 14.09 | 6.04 | 2.24 | 2.63 | 0.63 | 5.04 | 40.32 | 2.51 |
| 380 | 2 | 10.40 | 5.64 | 16.32 | 3.37 | 2.96 | 2.43 | 1.31 | 8.04 | 47.72 | 3.44 |

Butanol Conversion and Product Selectivity Data for Example.

x is any number from 0 to less than 0.5;
y is any number between 0 and 1 inclusive;
z is any number between 0 and 1 inclusive;
and w+x+y+z=1
with a base at a treatment temperature from about 25° C. to about 300° C. for a treatment time of about 1 minute to about 24 hours, and optionally washing the base-treated catalyst composition with a minimal amount of water.

3. The process of claim 1 or 2, wherein the base comprises an aqueous solution of a metal hydroxide Q(OH)$_f$ where f is 1 to 3 inclusive and Q is at least one metal selected from the group consisting of Li, Na, K, Rb, Cs, Sc, Y, Lu, Ti, V, Cr, Mn, Fe, Co, Ni, Cu, Zn, Zr, Nb, Mo, Ru, Rh, Pd, Ag, Hf, Ta, W, Re, Os, Ir, Pt, Au, La, Ce, Pr, Nd, Sm, Eu, Gd, Tb, Dy, Ho, Er, Tm, and Yb, and wherein the aqueous solution has a pH greater than about 11.

4. The process of claim 1 or 2, wherein the aqueous solution has a pH great than about 11.

5. The process of claim 1 or 2, wherein the initial catalyst composition further comprises a metal phosphate of Formula (II):

$$(M_a M'_b M''_c M'''_d)_3 (PO_4)_2 \qquad \text{(II)}$$

where
M is Mg;
M' is Ca;
M'' is Sr;
M''' is Ba;
a is any number between 0 and 1 inclusive;
b is any number between 0 and 1 inclusive;
c is any number between 0 and 1 inclusive;
d is any number between 0 and 1 inclusive;
and a+b+c+d=1.

6. The process of claim 1 or 2, wherein the initial catalyst composition further comprises at least one metal or metal ion selected from the group consisting of Li, Na, K, Rb, Cs, Sc, Y, Lu, Ti, V, Cr, Mn, Fe, Co, Ni, Cu, Zn, Zr, Nb, Mo, Ru, Rh, Pd, Ag, Hf, Ta, W, Re, Os, Ir, Pt, Au, La, Ce, Pr, Nd, Sm, Eu, Gd, Tb, Dy, Ho, Er, Tm, and Yb.

7. The process of claim 1 or 2, wherein the initial catalyst composition further comprises at least one anionic additive selected from the group consisting of carbonate, silicate, aluminate, arsenate, vanadate, sulfate, and borate.

8. The process of claim 1, wherein m is 0; n is any number between 0 and 1 inclusive; p is any number between 0 and 1 inclusive; and q is 0.

9. The process of claim 2, wherein w is 0; x is any number between 0 and 1 inclusive; y is any number between 0 and 1 inclusive; and z is 0.

10. A process comprising the step of:
contacting a reactant comprising 1-butanol with a catalyst composition under suitable reaction conditions to produce a reaction product comprising 2-ethylhexanol;
wherein the suitable reaction conditions include a temperature of about 350° C. to about 425° C. and a pressure from about 0.1 MPa to about 20.7 MPa; and
wherein the catalyst composition comprises a hydroxyapatite of Formula (I):

$$(M_w M'_x M''_y M'''_z)_5 (PO_4)_3 (OH) \qquad \text{(I)}$$

wherein
M is Mg;
M' is Ca;
M'' is Sr;
M''' is Ba;
w is any number between 0 and 1 inclusive;
x is any number from 0 to less than 0.5;
y is any number between 0 and 1 inclusive;
z is any number between 0 and 1 inclusive;
and w+x+y+z=1.

11. The process of claim 10, wherein the catalyst composition further comprises a metal phosphate of Formula (II):

$$(M_a M'_b M''_c M'''_d)_3 (PO_4)_2 \qquad \text{(II)}$$

where
M is Mg;
M' is Ca;
M'' is Sr;
M''' is Ba;
a is any number between 0 and 1 inclusive;
b is any number between 0 and 1 inclusive;
c is any number between 0 and 1 inclusive;
d is any number between 0 and 1 inclusive;
and a+b+c+d=1.

12. The process of claim 10, wherein the catalyst composition further comprises at least one metal or metal ion selected from the group consisting of Li, Na, K, Rb, Cs, Sc, Y, Lu, Ti, V, Cr, Mn, Fe, Co, Ni, Cu, Zn, Zr, Nb, Mo, Ru, Rh, Pd, Ag, Hf, Ta, W, Re, Os, Ir, Pt, Au, La, Ce, Pr, Nd, Sm, Eu, Gd, Tb, Dy, Ho, Er, Tm, and Yb.

13. The process of claim 10, wherein the catalyst composition further comprises at least one anionic additive selected from the group consisting of carbonate, silicate, aluminate, arsenate, vanadate, sulfate, and borate.

14. The process of claim 10, wherein w is 0; x is any number between 0 and 1 inclusive; y is any number between 0 and 1 inclusive; and z is 0.

\* \* \* \* \*